US009764021B2

(12) United States Patent
Ilg et al.

(10) Patent No.: US 9,764,021 B2
(45) Date of Patent: Sep. 19, 2017

(54) METHODS OF USING SALMONELLA ENTERICA PRESENTING C. JEJUNI N-GLYCAN OR DERIVATIVES THEREOF

(71) Applicant: EIDGE-NOESSISCHE TECHNISCHE HOCHSCHULE ZURICHE, Zurich (CH)

(72) Inventors: Karin Ilg, Zurich (CH); Markus Aebi, Wettingen (CH); Umesh Ahuja, Los Angeles, CA (US); Saba Amber, Los Angeles, CA (US); Flavio Schwartz, Zurich (CH)

(73) Assignee: EIDGENOESSISCHE TECHNISCHE HOCHSCHULE ZURICH, Zurich (CH)

( * ) Notice: Subject to any disclaimer, the term of this patent is extended or adjusted under 35 U.S.C. 154(b) by 0 days.

(21) Appl. No.: 15/094,537

(22) Filed: Apr. 8, 2016

(65) Prior Publication Data

US 2016/0213770 A1    Jul. 28, 2016

Related U.S. Application Data

(62) Division of application No. 13/254,232, filed as application No. PCT/EP2010/001884 on Mar. 25, 2010, now Pat. No. 9,309,493.

(30) Foreign Application Priority Data

Mar. 27, 2009  (EP) ...................................... 9004445

(51) Int. Cl.
| | | |
|---|---|---|
| *A01N 63/00* | (2006.01) | |
| *A61K 39/02* | (2006.01) | |
| *A61K 39/112* | (2006.01) | |
| *C12N 1/20* | (2006.01) | |
| *C12N 1/36* | (2006.01) | |
| *A61K 39/00* | (2006.01) | |

(52) U.S. Cl.
CPC ........ *A61K 39/105* (2013.01); *A61K 39/0275* (2013.01); *C12N 1/20* (2013.01); *C12N 1/36* (2013.01); *A61K 2039/522* (2013.01); *A61K 2039/523* (2013.01); *A61K 2039/542* (2013.01); *A61K 2039/55* (2013.01); *A61K 2039/552* (2013.01)

(58) Field of Classification Search
CPC .................................................. A61K 39/105
See application file for complete search history.

(56) References Cited

FOREIGN PATENT DOCUMENTS

WO  PCT/CA2003/001156     7/2004
WO  PCT/EP2006/004397     5/2006

OTHER PUBLICATIONS

International Search Report issued Jun. 18, 2010 for related application PCT/EP2010/001884.
Wysczynska, A., et al., Oral immunization of chickens with avirulent *Salmonella* vaccine strain carrying C. jejuni 72Dz/92 cjaA gene elecits specific humoral immune response associated with protection against challenge with wild-type Campylobacter, Vaccine, vol. 22, No. 11-12, Mar. 29, 2004, pp. 1379-1389.
Sizemore, D R, et al: "Live, attenuated *Salmonella* typhimurium vectoring Campylobacter antigens", Vaccine, vol. 24, No. 18, May 1, 2006 (May 1, 2006), pp. 3793-3803.
U.S. Appl. No. 09/122,441, filed Jul. 24, 1998, Megan Health, Inc.
Wacker, Michael, et al: "Substrate specificity of bacterial oligosaccharyltransferase suggests a common transfer mechanism for the bacterial and eukaryotic systems", Proceedings of The National Academy of Sciences of The United States of America, vol. 103, No. 18, May 2006 (May 2006).
Hoare, Anilei, et al: "The outer core lipopolysaccharide of *Salmonella enterica* serovar Typhi is required for bacterial entry into epithelial cells.", Infection and Immunity, vol. 74, No. 3, Mar. 2006 (Mar. 2006).
Wang, L. et al: "C-terminal half of *Salmonella,enterica*WbaP(RfbP) is the galactosyl-1-phosphate transferase domain catalyzing the first step of 0-antigen synthesis", Journal of Bacteriology, vol. 178, No. 9, May 1, 1996 (May 1, 1996), pp. 2598-2604.
Saldias, Soledad, et al: "Distinct functional domains of the *Salmonella enterica*WbaPtransferase that is involved in the initiation reaction for synthesis of the 0 antigen subunit", Microbiology (Reading), vol. 154, No. Part 2, Feb. 2008 (Feb. 2008), pp. 440-453.
Wacker, M. et al: "N-linked glycosylation in Campylobacter jejuni and its functional transfer into *E. coli* ", Science, vol. 298, Nov. 29, 2002 (Nov. 29, 2002), pp. 1790-1793.
Mario, Feldman, et al: "Engineering N-linked protein glycosylation with diverse 0 antigen lipopolysaccharide structures in *Escherichia coli*" Proceedingsof the Nationalacademyof Sciencesof The United States, vol. 102, No. 8, Feb. 22, 2005 (Feb. 22, 2005), pp. 3016-3021.
Linton, Dennis, et al: "Functional analysis of the Campylobacter jejuni N-linked protein glycosylation pathway" Molecular Microbiology, vol. 55, No. 6, Mar. 2005 (Mar. 2005), pp. 1695-1703.
Szymanski, Christine M., et al: "Campylobacter: A tale of two protein glycosylation systems." Trends in Microbiology, vol. 11, No. 5, May 2003 (May 2003), pp. 233-238.
Young N. M. et al: "Structure of the N-linked glycan present on multiple glycoproteins in the gram-negative bacterium, Campylobacter jejuni" Journal of Biological Chemistry, American Society for Biochemistry and Molecular Biology, vol. 277, No. 45, Nov. 8, 2002 (Nov. 8, 2002), pp. 42530-42539.
Szymanski, C M, et al: "Evidence for a Systemofgeneralproteinglycosylation in Campylobacter Jejuni" Molecular Microbiology, vol. 32, No. 5, Jan. 1, 1999 (Jan. 1, 1999), pp. 1022-1030.

(Continued)

*Primary Examiner* — Albert Navarro
(74) *Attorney, Agent, or Firm* — Juneau & Mitchell (57) ABSTRACT

The present invention relates to *Salmonella enterica* comprising at least pgl operon of *Campylobacter jejuni* or a functional derivative thereof and presenting at least one N-glycan of *Campylobacter jejuni* or N-glycan derivative thereof on its cell surface and, in particular, to medical uses and pharmaceutical compositions thereof as well as methods for treating and/or preventing *Campylobacter* and optionally *Salmonella* infections and methods for producing these *Salmonella* strains.

4 Claims, 4 Drawing Sheets

(56) References Cited

OTHER PUBLICATIONS

Fry, B N, et al: "The Lipopolysaccharide Biosynthesis Locus of Campylobacter Jejuni 81116" Microbiology, vol. 144, No. 8, Aug. 1, 1998. (Aug. 1, 1998), pp. 2049-2061.

METHODS OF USING *SALMONELLA ENTERICA* PRESENTING *C. JEJUNI* N-GLYCAN OR DERIVATIVES THEREOF

SEQUENCE LISTING

The instant application contains a Sequence Listing which has been submitted in ASCII format via EFS-Web and is hereby incorporated by reference in its entirety. Said ASC II copy, created on Dec. 2, 2011, is named RIT-232U.txt and is 2,632 bytes in size.

CROSS REFERENCE TO RELATED APPLICATIONS

Applicant claims priority to co-pending U.S. patent application Ser. No. 13/254,232, filed Dec. 5, 2011, and thereby to International Patent Application PCT/EP2010/001884, filed Mar. 25, 2010 and thereby to European Patent Application 9004445.4, filed Mar. 27, 2009.

FIELD OF THE INVENTION

The present invention relates to *Salmonella enterica* comprising at least one pgl operon of *Campylobacter jejuni* or a functional derivative thereof and presenting at least one N-glycan of *Campylobacter jejuni* or N-glycan derivative thereof on its cell surface. In addition, it is directed to medical uses, pharmaceutical compositions, food and feed additives made thereof as well as methods for treating and/or preventing *Campylobacter* infections, in particular those caused by *C. jejuni, C. lari, C. coli, C. upsaliensis*, and *C. fetus*, and optionally *Salmonella* infections and methods for producing these *Salmonella* strains.

RELEVANT BACKGROUND OF THE INVENTION

*Campylobacter jejuni* (*C. jejuni*) is a food-borne pathogen that is the leading cause of human acute gastroenteritis in developed countries. Its regular hosts are live stock, in particular chicken and cattle. Infection with *C. jejuni* is also associated with several long-term consequences, the most severe being the autoimmune diseases Miller-Fisher syndrome and Guillain-Barré syndrome. These are evoked by antibodies of the mammalian host against the mimicry of mammalian ganglioside structures on the surface of the pathogen which then also attack the host's own gangliosides. This molecular mimicry is one of the reasons why there are currently no efficient vaccines against *C. jejuni* available because it excludes the use of attenuated or killed *C. jejuni* cells as vaccines.

US Patent 2007/065461 teaches a vaccine composed of at least one capsular polysaccharide (CPS) of *C. jejuni* optionally linked in vitro to a carrier protein. Injection of this conjugate into mice and apes protected against later intranasal challenge with *C. jejuni*. Production of this vaccine requires isolation and purification of the CPS as well as chemical linkage to the carrier protein and further purification steps.

Poly et al. (Infection and Immunity, 75:3425-3433, 2008) describe *C. jejuni* strains lacking the ganglioside mimicry structures that are currently tested as vaccine candidates.

Once glycosylation was considered to be specifically a eukaryotic phenomenon but was later shown to be widespread in both the Archaea and Eubacteria domains. Bacterial O- and N-linkages are formed with a wider range of sugars than those observed in eukaryotic glycoproteins. Glycosidic N-glycosylation of proteins in procaryotes was first demonstrated in *C. jejuni*. (Szymanski et al., Molecular Microbiology 32:1022-1030, 1999). The glycosylation machinery of *C. jejuni* has been characterized and has even been successfully transferred to *E. coli*, where active N-glycosylation of proteins was demonstrated (Wacker et al., Science, 298:1790-1793, 2002). The gene locus of *C. jejuni* termed pgl (for protein glycosylation) is involved in the glycosylation of multiple proteins. Its mutational silencing results in loss of immunogenicity in multiple proteins.

US patent application 2006/0165728 A1 identifies a specific and highly immunogenic heptasaccharide that is common to at least several *Campylobacter* species and numerous strains that are important as human and veterinary pathogens. The heptasaccharide has the following formula (I):

GalNAc-a1,4-GalNAc-a1,4-[Glc-β-1,3]GalNAc-a1,4-
Gal-NAc-a1,4-GalNAc-a1,3-Bac, wherein Bac (also termed bacillosamine) is 2,4-diacetamido-2,4,6-trideoxy-D-glucopyranose, GalNAc is N-Acetyl-galactosamine and Glc is glucose. This glycan moiety is a component of multiple glycoproteins. In *C. jejuni* the N-glycan is important for the interaction of *C. jejuni* with host cells. Mutations in the glycosylation machinery lead to decreased colonization of intestinal tracts in mice. Furthermore, pharmaceutical compositions comprising either (i) said heptasaccharide or a conjugate thereof or (ii) an antibody directed against said heptasaccharide are suggested for vaccination use in live stock, specifically in poultry.

The genus *Salmonella* is a member of the family Enterobacteriaceae. The genus is composed of Gram-negative bacilli that are facultative anaerobic and flagellated (motile). They possess three major antigens, the "H" or flagellar antigen, the "0" or somatic antigen (part of the LPS moiety) and the "Vi" or capsular antigen (referred to as "K" in other Enterobacteriaceae). Salmonellae also possess the LPS endotoxin characteristic of Gram-negative bacteria. LPS is composed of three domains: The lipid A part, also known as endotoxin, anchors LPS molecules in the outer membrane with its fatty acid chains. It is connected through the inner core consisting of heptoses and KDO (3-deoxy-D-mannooctulosonic acid) with the outer core containing hexoses and N-acetylhexoses. Linked to the last glucose of the outer core is the polymeric O-antigen region. This region is composed of 16 to >100 repeats of an oligosaccharide structure containing four to six monosaccharides. The endotoxic lipid A part evokes fever and can activate complement, kinin and clotting factors.

For some time *Salmonella* strains have been of interest for producing and presenting bacterial immunogens. For example, the genes encoding the enzymes for the biosynthesis of O-antigen of *Shigella* were genomically integrated into an aroA vaccination strain of *Salmonella enterica* serovar *Typhimurium*, which then produced a hybrid LPS (Fait et al., Microbial Pathogenesis 20:11-30, 1996). Also, clusters necessary for O-antigen biosynthesis of *Salmonella dysenteriae* were cloned into a stable expression vector, which was then transferred into the typhoid fever vaccination strain Ty21a. The resulting strain produces hybrid LPS and induces protective immunity against challenge with *S. dysenteriae* (DE Qui Xu et al., Vaccine 25: 6167-6175, 2007).

U.S. Pat. No. 6,399,074 B1 discloses a life attenuated *Salmonella* vaccine for protecting birds against infection by avian pathogenic gram-negative microbes. The vaccine is a recombinant *Salmonella* strain expressing the O-antigen of an avian pathogenic gram-negative microbe such as *E. coli* 078 that is pathogenic in poultry. The recombinant *Salmonella* strain does not express *Salmonella* O-antigen due to a mutation in the O-antigen polymerase rfz (new gene nomenclature wzy).

In view of the above prior art it is the objective of the present invention to provide an effective and safe, easily mass-produced, long-acting and cheap vaccine composition for preventing and/or treating *Campylobacter* infections in humans and animals, in particular in live stock, more particular in poultry.

This objective is solved by providing in a first aspect a *Salmonella enterica* that comprises at least one pgl operon of *Campylobacter jejuni* or a functional derivative thereof and presents at least one N-glycan of *Campylobacter jejuni* or N-glycan derivative thereof on its cell surface.

The *Salmonella* strain useful for the present invention can be any strain that is or can be sufficiently attenuated to allow for its non-pathological administration to humans and/or animals in life and/or dead form. Preferred *Salmonella* strains are *Salmonella enterica* strains selected from the group consisting of *Salmonella Typhimurium, enteriditis, heidelberg, hadar, agona, kentucky, typhi* and *infantis*, more preferably *Salmonella enterica* serovar *Typhimurium* strains. *Salmonella Typhimurium* is especially useful for vaccination purposes because the genome sequence is fully characterized and many animal studies confirm its safe medical use.

The term "pgl operon" as used herein refers to any physiologically active N-glycosylation cluster of *C. jejuni* genes capable of N-glycosylating homologous or heterologous structures produced by the *Salmonella* strain of the invention. The pgl operon in *C. jejuni* encodes all enzymes necessary for the synthesis of the *C. jejuni* N-glycan heptasaccharide, its transport through the inner membrane and the transfer to proteins. PglD, E, F code for the enzymes involved in bacillosamine biosynthesis, PglC transfers phosphorylated bacillosamine to undecaprenylphosphate and PglA, H and J add the GalNAc residues. The branching Glc is attached by PglI. The transfer of the completed heptasaccharide occurs through action of PglK and the oligosaccharyltransferase PglB transfers the N-glycan to protein.

A functional derivative of a pgl operon is a cluster of genes derived from any *C. jejuni* pgl operon having deletions, mutations and/or substitutions of nucleotide(s) or whole genes but still capable of producing a linkable oligo- or polysaccharide that can be linked to homologous or heterologous structures produced by the *Salmonella* strain of the invention. One or more pgl operons or derivatives thereof can be integrated into the chromosome of the *Salmonella* strain or it/they can be introduced as part of at least one plasmid. Chromosomal integration is preferred because it is more stable compared to plasmid vectors, the loss of which could occur during propagation. It is noted that the *Salmonella* strain of the invention may comprise more than one pgl operon or derivative thereof producing one or more N-glycans or derivative(s) thereof. As a matter of fact, it is preferred that the strain of the invention has more than one type of pgl operon resulting in more than one N-glycan structure, which can be of advantage for eliciting a more diverse immune response in a human or animal against different *C. jejuni* strains.

It is also noted that the expression level of the *C. jejuni* N-glycan can optionally be regulated by the use of different promoters upstream of the pgl operon, including, but not limited to, promoters of ribosomal protein genes, e.g. spc or rpsm as well as promoters from antibiotic-resistance encoding genes like bla or similar and preferably strong promoters. This type of regulation is available for plasmid-encoded or genomically integrated pgl operons. Furthermore, plasmid stability can optionally be enhanced by including essential genes on the plasmid while deleting these genes in the genome of the *Salmonella* strain of the invention. Preferred targets encompass for example the genes encoding the tRNA-transferases like CysS.

In a preferred embodiment, the *Salmonella* strain of the invention is one comprising at least one pgl operon, wherein one or more genes for bacillosamine biosynthesis are inactivated by mutation and/or partial or complete deletion, preferably by partial and/or complete deletion of the genes D, E, F, G. In a most preferred embodiment the pglE, F and G genes of the pgl operon are completely deleted and the pglD gene is partially deleted, for example the pglD open reading frame (ORF) terminates after 270 base pairs (the full length ORF contains 612 base pairs).

In a further preferred embodiment the pglB gene of the pgl operon is inactivated, meaning that the corresponding oligosaccharyltransferase B is either not expressed or at least enzymatically inactivated. The pglB gene product transfers the N-glycan to a specific polypeptide acceptor site further described below. Inactivation of the transferase leads to the N-glycan or N-glycan derivative being exclusively bound to the O-antigen acceptor lipid A core in *Salmonella*.

In a most preferred embodiment the pgl derivative is one, wherein one or more genes for bacillosamine biosynthesis, pg D, E, F, G, and transfer are inactivated and the pglB gene is inactivated, too. This embodiment leads to the exchange of GlcNAc for bacillosamine resulting in increased cellular presentation as well as to transfer of the modified heptasaccharide to lipid A core instead of to polypeptide acceptors.

The at least one N-glycan of *C. jejuni* or N-glycan derivative thereof can be any N-glycan produced by any pgl operon of *Campylobacter jejuni* or a functional derivative thereof. It is of course preferred that the N-glycan is still immunogenic, i.e. elicits an immune response specific for *C. jejuni*.

In a preferred embodiment, the N-glycan is the heptasaccharide of formula (I) as described above, i.e. GalNAc-α1,4-GalNAc-α1,4-[Glc-β-1,3]GalNAc-α1,4-Gal-NAc-α1,4-GalNAc-α1,3-Bac, wherein Bac (also termed bacillosamine) is 2,4-diacetamido-2,4,6-trideoxy-D-glucopyranose.

The preferred pgl operon, wherein the genes for bacillosamine biosynthesis are inactivated, preferably mostly or completely deleted, leads to the synthesis of an N-glycan derivative, i.e. the heptasaccharide of formula (II), being GalNAc-α1,4-GalNAc-α1,4-[Glc-β-1,3]GalNAc-α1,4-Gal-NAc-α1,4-GalNAc-α1,3-GlcNAc.

Surprisingly, the N-glycan derivative of formula (II) is presented in higher amounts than the N-glycan of formula (I) on the cells surface of the *Salmonella* strains of the present invention and is also immunogenic. This is experimentally confirmed in the example section below.

In a preferred embodiment the N-glycan(s) or derivative(s) resulting from the at least one pgl operon or derivative thereof can be linked to at least one homologous or heterologous *Salmonella* polypeptide that will eventually be transferred to and presented on the cell surface. Preferably the at least one N-glycan or N-glycan derivative is linked to a polypeptide comprising at least one consensus sequon N-Z-S/T (see Nita-Lazar M et al., Glycobiology. 2005; 15(4):361-7), preferably D/E-X-N-Z-S/T (SEQ ID NO: 1), wherein X and Z may be any natural amino acid except Pro (see Kowarik et al. EMBO J. 2006; 25(9):1957-66).

The polypeptide linked to the N-glycan (derivative) may be any type of polypeptide such as a pure polypeptide (only amino acids) or a posttranslationally modified polypeptide, e.g. a lipid-linked polypeptide.

For heterologous polypeptides as carriers of the N-glycan(s) (derivatives) it is preferred that they comprise the signal sequence MKKILLSVLTTFVAVVLAAC (SEQ ID NO: 2) directing the N-linked conjugate to the outer membrane of the cell and wherein the LAAC motif (SEQ ID NO: 3) is used for acylation of the cysteine residue, which anchors the polypeptide in the outer membrane (see also Kowarik et al., EMBO J. May 3; 25(9):1957-66, 2006).

In the most preferred embodiment the at least one N-glycan or derivative thereof resulting from the at least one pgl operon or derivative thereof is linked to the *Salmonella* lipid A core or a functionally equivalent derivative thereof. The Lipid A core of *Salmonella* is an oligosaccharide structure consisting of hexoses, N-acetylhexoses, heptoses and KDO (3-deoxy-D-manno-octulosonic acid) linked through two glucosamines to six fatty acid chains anchoring the structure in the outer membrane of the bacterium. A functionally equivalent derivative of the lipid A core is one capable of accepting one or more glycans or derivatives thereof and presenting them on the cell surface. It is noted that in this case the N-glycan or derivative thereof is not N-linked because the *Salmonella* structure lipid A is not a polypeptide. The N-glycan is preferably linked to GlcII in the lipid A core or a functional derivative thereof.

Preferably the at least one N-glycan or derivative thereof takes the place of the O-antigen side chains in LPS (lipopolysaccharide). The inner and outer lipid A core of *Salmonella* remains unchanged while O-antigen biosynthesis is abolished through mutation of wbaP. The N-glycan is then transferred by the O-antigen ligase WaaL and linked to the GlcII residue of the lipidA outer core oligosaccharide structure.

It is preferred and for medical uses highly important that the *Salmonella* strain of the invention does not elicit pathogenic effects when administered to an animal or human in live and/or inactivated form. The skilled person is aware of many ways of attenuating virulent *Salmonella* species by mutation. Preferred mutations for attenuating *Salmonella* strains for use in the present invention are selected from the group consisting of pab, pur, aro, aroA, asd, dap, nadA, pncB, galE, pmi, fur, rpsL, ompR, htrA, hemA, cdt, cya, crp, phoP, phoQ, rfc, poxA and galU. One or more of these mutations may be present. Mutations aroA, cya and/or crp are more preferred.

The O-antigen biosynthesis genes of *Salmonella* are clustered in the rfb locus, a hypervariable DNA region of the *Salmonella* chromosome. Partial or full inactivation has been associated with attenuation of *Salmonella* strains. On the other hand, the O-antigen is also an important antigenic determinant for inducing immunity in a host.

In a particularly preferred embodiment the *Salmonella* strain of the present invention is attenuated by partial or full inactivation of the expression of the O-antigen, preferably by one or more mutations and/or deletions in the rfb gene cluster, more preferably in the wbaP gene, most preferably deletion of the wbaP gene.

It is understood that as used herein the terms "rfb locus" and "wbaP gene" are meant to encompass any corresponding locus and gene in any *Salmonella* strain that is capable of expressing O-antigen or related antigens.

The wbaP gene product is the phosphogalactosyltransferase which starts O-antigen biosynthesis by adding phosphogalactose to undecaprenylphosphate. Its inactivation/deletion leads to complete abolishment of the O-antigen synthesis, the sugar product of which competes with the N-glycan(s) (derivatives) of *C. jejuni* for the lipid carrier undecaprenylphosphate and for the transfer by ligase WaaL. pgl locus-induced protein N-glycosylation and wzy-dependent O-antigen synthesis in bacteria are homologous processes. It was found that the *Salmonella* O-antigen ligase WaaL has relaxed substrate specificity and that it can transfer *C. jejuni* N-glycan to *Salmonella* lipid A core.

Hence, in a most preferred embodiment the *Salmonella* strain of the invention is mutated in the wbaP gene inactivating the phosphogalactosyltransferase enzyme. It is noted that this type of O-antigen inactivation has not been described before for vaccination purposes and is superior to presently known O-antigen negative mutants, because it is genetically defined and allows for increasing the amount of *C. jejuni* N-glycans (derivatives) presented on the cell surface of *Salmonella* strains.

Therefore and as an independent invention, the present invention also relates to a *Salmonella* strain mutated, preferably deleted, and thus inactivated in the wbaP gene, that is useful for vaccine uses of *Salmonella* strains as such as well as *Salmonella* strains as carriers of heterologous antigens, preferably glycosylated, more preferably N-glycosylated antigens.

In a most preferred embodiment the invention is directed to *Salmonella enterica*, preferably a serovar *typhimurium* strain, that
(a) comprises
  (i) at least one pgl operon of *Campylobacter jejuni* or a functional derivative thereof, preferably at least one pgl operon, wherein one or more genes for bacillosamine biosynthesis are inactivated and
  (ii) mutations and/or deletions in the wbaP gene leading to complete inactivation of O-antigen biosynthesis,
(b) and presents at least one N-glycan of *Campylobacter jejuni* or N-glycan derivative thereof, preferably (I) GalNAc-a1,4-GalNAc-a1,4-[Glc-β-1,3]GalNAc-a1,4-GalNAc-a1,3-2,4-diacetamido-2,4,6-trideoxy-D-glucopyranose and/or (II) GalNAc-a1,4-GalNAc-a1,4-[Glc-β-1,3]GalNAc-a1,4-Gal-NAc-a1,4-GalNAc-a1,3-GlcNAc on its cell surface.

The above-described *Salmonella* strains of the invention are highly immunogenic and produce immune responses against *C. jejuni* infections. Furthermore, once prepared they can be easily propagated and mass-produced. As an add-on advantage the administration thereof to an animal or human provides immunity against *C. jejuni* and *Salmonella* infections. They can be administered as dead or live vaccines, live vaccines allowing for prolonged propagation and sustained immune stimulus in the host as well as full immune responses without adjuvants.

Therefore, the present invention also relates to the medical use of live or dead *Salmonella* strains of the present invention, in particular for preparing a medicament, preferably a vaccine.

Preferably, the medicament is useful for the prevention and/or treatment of *Campylobacter jejuni* and optionally *Salmonella* infections, preferably infections in life stock, more preferably in cattle and poultry, most preferably in poultry such as chicken, turkey, goose and ducks.

A third aspect of the present invention relates to a pharmaceutical composition, food or feed (additive) comprising dead or live *Salmonella enterica* of the present invention and a physiologically acceptable excipient.

For example, a pharmaceutical composition of the present invention can be prepared by medium or large scale growth of *Salmonella* strains of the invention containing either the at least one plasmid-encoded or chromosome-integrated pgl operon or derivative thereof. These *Salmonella* can be used directly or be formulated to accommodate the specific target human or animal and the specific route of administration. Pharmaceutical compositions comprising live *Salmonella* are preferred for obvious reasons.

Alternatively, the invention relates to a food or feed for humans or animals, preferably life stock, more preferably poultry, comprising dead or live *Salmonella enterica* of the present invention and a physiologically acceptable excipient and/or food stuff. For example, such a feed would greatly reduce *C. jejuni* colonisation of poultry flocks and consequently decrease the chance of human infections by *C. jejuni* and also *Salmonella* infections through contaminated meat.

A fourth aspect of the present invention is directed to a method for treating and/or preventing *C. jejuni* and optionally *Salmonella* infections, comprising administration of a *Salmonella enterica*, pharmaceutical composition, food or feed of the present invention to a human or animal in need thereof in a physiologically active amount.

For therapeutic and/or prophylactic use the pharmaceutical compositions of the invention may be administered in any conventional dosage form in any conventional manner. Routes of administration include, but are not limited to, intravenously, intramuscularly, subcutaneously, intranasally, intrasynovially, by infusion, sublingually, transdermally, orally (e.g. gavage), topically or by inhalation. The preferred modes of administration are oral, intravenous and intranasal, oral and intranasal being most preferred.

The *Salmonella* of the invention may be administered alone or in combination with adjuvants that enhance stability and/or immunogenicity of the bacteria, facilitate administration of pharmaceutical compositions containing them, provide increased dissolution or dispersion, increase propagative activity, provide adjunct therapy, and the like, including other active ingredients.

Pharmaceutical dosage forms of the *Salmonella* described herein include pharmaceutically acceptable carriers and/or adjuvants known to those of ordinary skill in the art. These carriers and adjuvants include, for example, ion exchangers, alumina, aluminium stearate, lecithin, serum proteins, buffer substances, water, salts, electrolytes, cellulose-based substances, gelatine, water, pretrolatum, animal or vegetable oil, mineral or synthetic oil, saline, dextrose or other saccharide and glycol compounds such as ethylene glycol, propylene glycol or polyethylene glycol, antioxidants, lactate, etc. Preferred dosage forms include tablets, capsules, solutions, suspensions, emulsions, reconstitutable powders and transdermal patches. Methods for preparing dosage forms are well known, see, for example, H. C. Ansel and N. G. Popovish, Pharmaceutical *Dosage Forms and Drug Delivery Systems*, 5th ed., Lea and Febiger (1990) and, in particular, Pastoret et al., Veterinary Vaccinology, Elsevier March 1999). Dosage levels and requirements are well-recognized in the art and may be selected by those of ordinary skill in the art from available methods and techniques suitable for a particular patient. As the skilled artisan will appreciate, lower or higher doses may be required depending on particular factors. For instance, specific doses and treatment regimens will depend on factors such as the patient's (human or animal) general health profile, the severity and course of the patient's disorder or disposition thereto, and the judgment of the treating physician or veterinarian.

In a preferred embodiment for oral vaccination the regimen consists of administration of *Salmonella* containing the pgl operon or derivative thereof either on plasmid or integrated into the chromosome on day 1 or 2 after hatch of the chicks with about $10^6$ cfu (colony forming units) per chick with a boost at days 14 or 21 after hatch with the same amount of bacteria. These two administrations will provide enough stimulation for the immune system to build up a response against *C. jejuni* N-glycan or derivatives thereof and also against *Salmonella* proteins to provide protection against later colonisation of the chickens. An alternative for vaccinating chicks is by intravenous injection of inactivated, e.g. heat-inactivated or formalin-inactivated bacteria at day 1 or 2 after hatch and a boost at day 14 or 21. As a further option, chicks may also be vaccinated only once at a later time point up to 3 weeks of age, either intravenously with heat-inactivated or formalin-inactivated bacteria or intragastrically with live bacteria.

Last but not least, the present invention is about a method of producing *Salmonella enterica* according to the invention, comprising the step(s) of (i) introducing into *Salmonella enterica*, preferably by at least one plasmid vector or by genomic integration, at least one pgl operon of *C. jejuni* or a functional derivative thereof, preferably at least one pgl operon, wherein one or more, preferably all genes for bacillosamine biosynthesis are inactivated, and (ii) preferably introducing mutations and/or deletions in the wbaP gene leading to complete inactivation of O-antigen biosynthesis.

In the following the present invention will be further illustrated with reference to specific embodiments and experiments which are not intended to be interpreted as limiting the scope of the invention as presented by the appended claims.

FIGURES

A) shows the transfer of *C. jejuni* N-glycan to an *S. Typhimurium* lipid A core in a strain producing O-antigen and featuring the pgl$_{mut}$ operon ("mut" means PglB is inactivated by 2 point mutations;

B) shows an *S. Typhimurium* ΔwbaP strain without any O-antigen and featuring a pgl3$_{mut}$ operon in which the genes for bacillosamine biosynthesis are deleted;

C) illustrates the deletions in the pgl3$_{mut}$ operon.

A) shows an anti-*C. jejuni* N-glycan immunoblot of a SDS-PAGE of *S. Typhimurium* wild type and ΔwbaP proteinase K-treated whole cell extracts of strains carrying the denoted plasmids and demonstrates display of *C. jejuni* N-glycan on *S. Typhimurium* lipid A core.

B) is a silver-stained SDS-PAGE (left panel) and an anti-*Salmonella* group B O-antigen immunoblot (right panel) of a SDS-PAGE of *S. Typhimurium* wild type and ΔwbaP whole cell extracts treated with proteinase K. It confirms the lack of polymeric O-antigen in the ΔwbaP strain.

C) shows an anti-*C. jejuni* N-glycan immunoblot of a SDS-PAGE of *S. Typhimurium* ΔwbaP strain with an integrated empty vector (control) or an integrated pgl3$_{mut}$ operon and proves expression of *C. jejuni* N-glycan on *S. Typhimurium* ΔwbaP lipid A core with an integrated pgl3$_{mut}$ operon.

D) depicts in the left panel an immunoblot using serum from a mouse infected intravenously with heat-killed *S. Typhimurium* ΔwbaP displaying *C. jejuni* N-glycan with GlcNAc at the reducing end and encoded by pgl3$_{mut}$. Recognition of *C. jejuni* wild type but not of *C. jejuni*

81-176pglB cells is evident. The right panel shows a Coomassie-stained SDS-PAGE of the samples used in the immunoblot analysis of the mouse sera.

FIG. 3 depicts the in vitro tests used to demonstrate the attenuation of *S. Typhimurium* ΔwbaP A) shows an increased sensitivity of *S. Typhimurium* ΔwbaP to complement in human serum: Complement-mediated killing of kanamycin-resistant serovar *Typhimurium* wild type strain, M939, O-antigen negative ΔwbaP::cat (SKI11) and complemented mutant ΔwbaP::pKI9 (SKI33) was tested by incubating a 1:1:1 mixture of wild type, ΔwbaP and ΔwbaP::pKI9 (SKI33) *Salmonella* for the indicated time points together with 20% human serum or 20% heat-inactivated human serum. Survival was analysed by plating on differentiating media.

B) depicts the the result of the experimental setting of A) but differing in the use of heat-inactivated serum instead. None of the strains are affected in survival.

C) illustrates the defect of *S. Typhimurium* ΔwbaP in swimming motility compared to *S. Typhimurium* wild type and non-motile strain fliGHI:Tn10.

A) grafically presents the competitive indices (CI; (mutant/wild type) output/(mutant/wild type) input) of serovar *Typhimurium* ΔwbaP (SKI12) and wild type determined at days 1-3 post infection in feces and at day 4 post infection in the cecal content demonstrating a reduced colonisation ability of *S. Typhimurium* ΔwbaP when compared to wild type.

B) CI in the mLN, spleens and livers at day 4 post infection.

EXAMPLES

Bacterial Strains and Growth Conditions

A summary of bacterial strains used for the experiments listed in the examples is provided in table 1. Bacteria were grown in Luria-Bertani (LB) medium (10 g/l Bacto tryptone, 5 g/l Bacto yeast extract, 5 g/l NaCl). LB agar plates were supplemented with 1.5% (w/v) agar. Antibiotics were used in the following final concentrations: Ampicillin (amp) 100 μg/ml, kanamycin (kan) 50 μg/ml, chloramphenicol (cam) 25 μg/ml, streptomycin (strep) 50 μg/ml, tetracycline (tet) 10 μg/ml.

Example 1—Display of *C. jejuni* N-glycan on the *Salmonella enterica* sv *Typhimurium* Lipid A Core Wzy-dependent O-antigen biosynthesis and *C. jejuni* N-glycan biosynthesis are homologous processes (Feldman et al., Proc. Natl. Acad. Sci. USA.; 102(8):3016-21, 2005) which both start with the assembly of an oligosaccharide structure on an undecaprenylpyrophosphate linker. The homology of the two pathways as well as the relaxed substrate specificity of the *S. enterica* sv. *Typhimurium* O-antigen ligase WaaL (Fait et al., Microbial Pathogenesis 20:11-30, 1996; De Qui Xu et al., Vaccine 25: 6167-6175, 2007) were explored for the possibility of combining the pathways to display the *C. jejuni* N-glycan on *Salmonella* lipid A core.

A plasmid containing the *C. jejuni* $pgl_{mut}$ operon with inactivated PglB (pACYCpgl$_{mut}$; Wacker et al 2002) was introduced into a *Salmonella enterica* serovar *Typhimurium* strain by electroporation. As negative control the corresponding empty vector pACYC184 was used.

The glycoconjugates of the transformants were tested for display of the *C. jejuni* N-glycan by SDS-PAGE and subsequent immunoblot with an anti-*C. jejuni* N-glycan antiserum (Amber 2008). Samples were prepared as follows: The equivalent of 2 $OD_{600}$/ml of log phase growing cultures of *S. enterica* sv *Typhimurium* containing either pACYC184 or pACYpgl$_{mut}$ was spun down at 16,000 g for 2 min and the supernatant was discarded. Cells were resuspended in 100 μl Lämmli sample buffer (0.065 M Tris-HCl pH 6.8, 2% SDS (w/v), 5% β-Mercaptoethanol (v/v), 10% Glycerin (v/v), 0.05% Bromophenol blue (w/v)) and lysed for 5 min at 95° C. After cooling to room temperature, proteinase K (Gibco/Life Technologies) was added (final concentration 0.4 mg/ml) and incubated 1 h at 60° C. before loading equal amounts on a 15% sodium dodecylsulfate polyacrylamide gel electrophoresis (SDS-PAGE). To detect *C. jejuni* N-glycan, a rabbit polyclonal antiserum against the *C. jejuni* N-glycan was used (S. Amber, PhD.—thesis, ETH Zürich, Department of Biological Science. Zurich, 2008). Visualisation of signals was carried out with goat-anti-rabbit-IgG-HRP conjugate (Santa Cruz) and ECL (Amersham) as recommended by the manufacturer.

Figure 1:
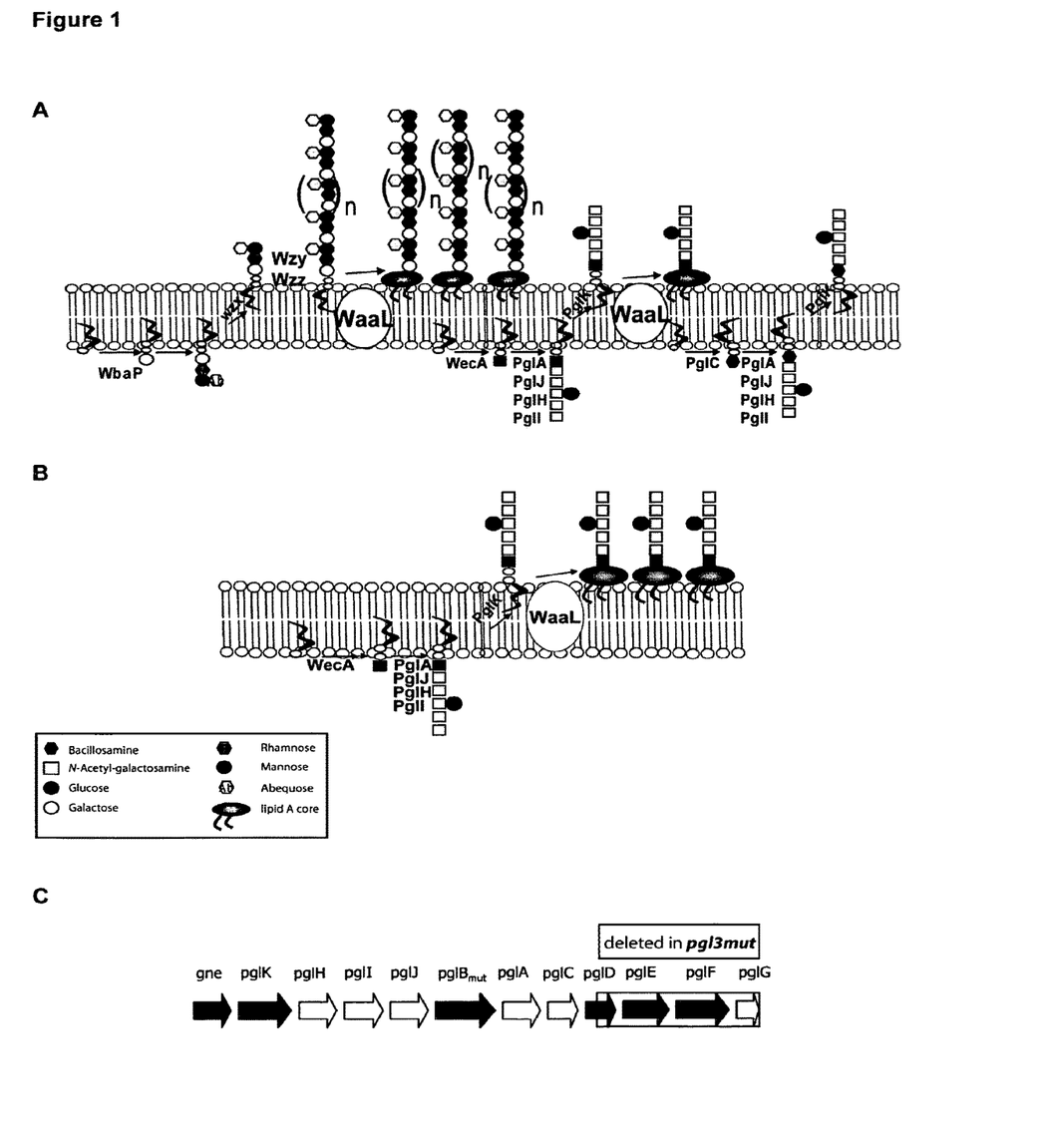
FIG. 1 is a schematic picture of a *C. jejuni* N-glycan display on *S. enterica* sv. *Typhimurium*.
Figure 2:
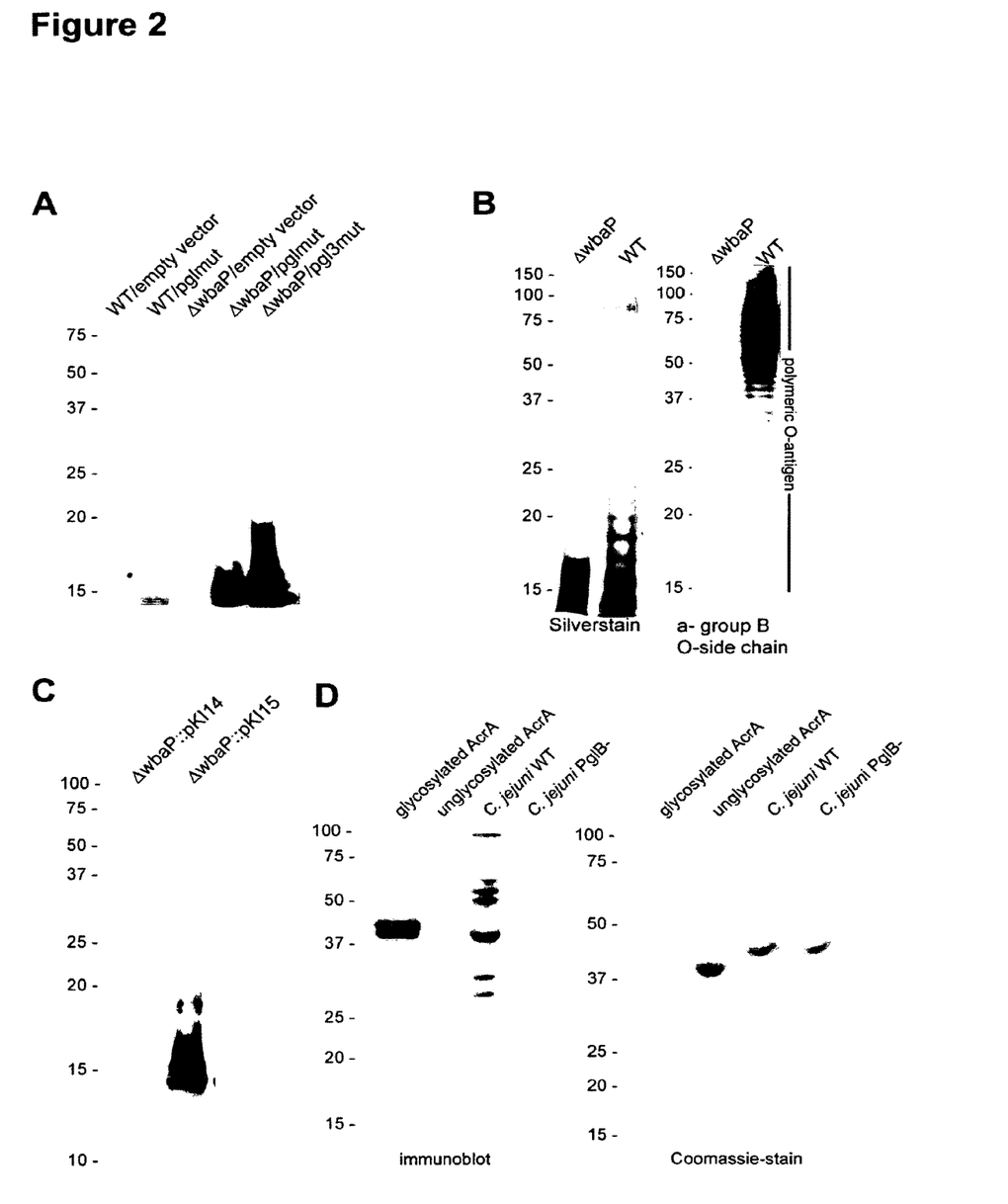
FIG. 2 demonstrates the display of *C. jejuni* N-glycans on *S. enterica* sv. *Typhimurium*
Figure 3:
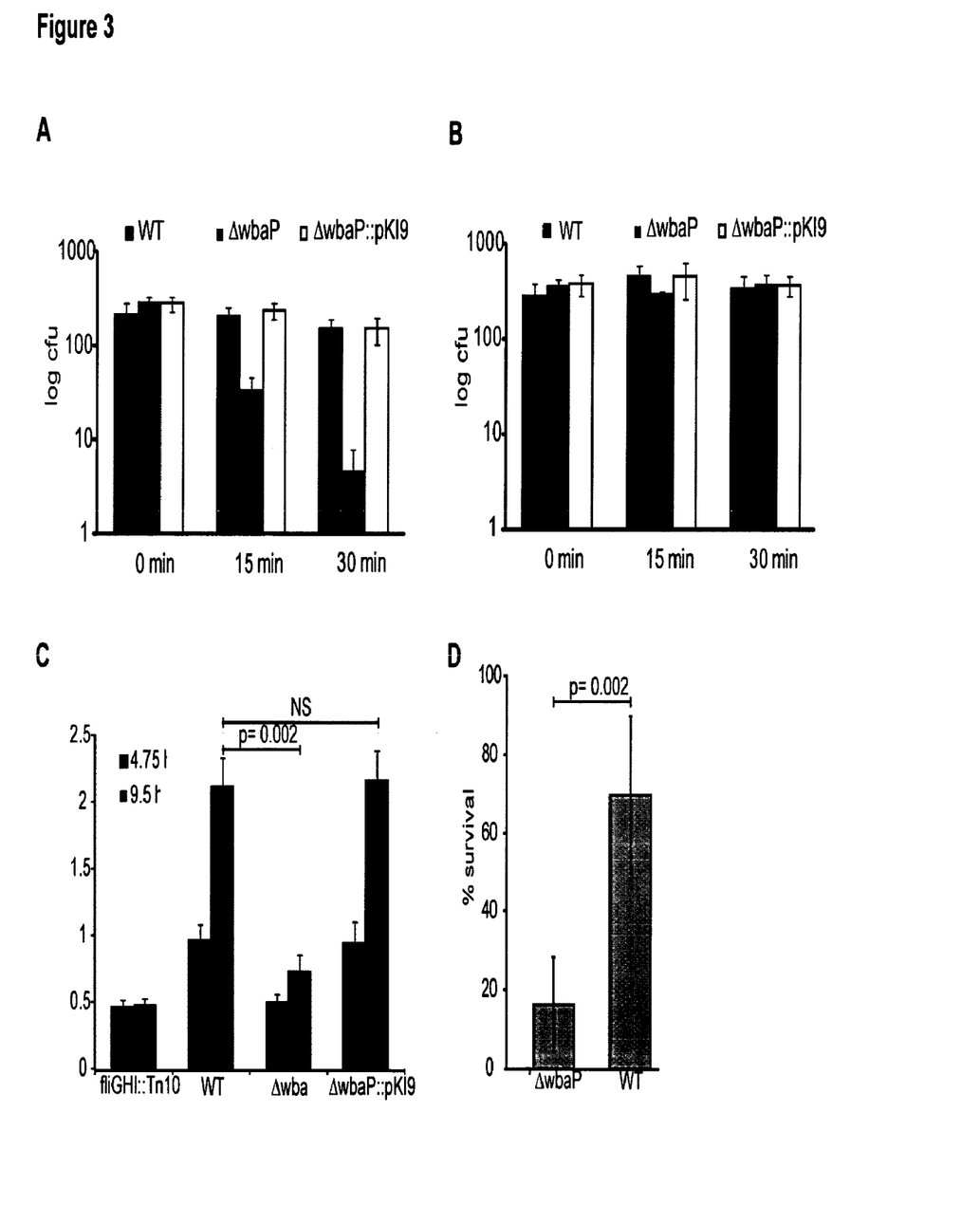

*C. jejuni* N-glycan could be detected on *S. enterica* sv. *Typhimurium* lipid A core when pACYCpgl$_{mut}$ was present in the cells (FIG. 2A lane 2) but not if the empty vector had been introduced into the cells (FIG. 2A lane 1). This shows that *S. enterica* sv *Typhimurium* WaaL transfers *C. jejuni* N-glycan from undecaprenylpyrophosphate to lipid A core.

Example 2—Construction of a wbaP Deletion in *Salmonella enterica* sv *Typhimurium* and Increased Display of *C. jejuni* N-Glycan in the O-Antigen Negative Strain Deletion of O-antigen biosynthesis was assumed to abolish competition between the O-antigen biosynthesis pathway and biosynthesis of the *C. jejuni* N-glycan for the lipid carrier undecaprenylphosphate.

Construction of a wbaP deletion mutant of *S. Typhimurium* wild type SL1344 was carried out as described (Datsenko and Wanner, PNAS USA 97(12): 6640-5, 2000). Primers RfbP H1P1 (for sequence see table 1) and RfbP H2P2 annealing to template DNA from plasmid pKD3, which carries a chloramphenicol-resistance gene flanked by FRT (FLP recognition target) sites were synthesised. These primers also contain 40 to 45 additional nucleotides corresponding to regions directly upstream and downstream of the wbaP gene. They were used to amplify a gene cassette for in frame deletion of wbaP as described (Datsenko and Wanner, see above). After arabinose-induced expression of the λ Red recombinase from plasmid pKD46 in *S. Typhimurium* wildtype strain SL1344 the recombinase exchanged the target gene with the chloramphenicol cassette of the PCR product introduced by electroporation. Transformants were selected by plating on chloramphenicol plates at 37° C. overnight and presence of the cat gene in the correct position in the genome was confirmed by PCR. The chloramphenicol resistant resulting clone (wbaP::cat) was termed SKI11. Removal of the chloramphenicol resistance cassette was possible by using pCP20 encoding the FLP recombinase recognising the flanking FRT regions and the resulting strain was termed SKI12 after verification by PCR (also see IIg, Endt et al., Inf. Immun., 77, 2568, June 2009).

Phenotypic analysis of the glycoconjugates of the resulting strain was performed by SDS-PAGE followed by subsequent staining of the glycoconjugates by silver. For SDS-PAGE, samples were prepared as follows: The equivalent of 2 OD$_{600}$/ml of log phase growing cultures of *S. Typhimurium* wild type or *S. Typhimurium* ΔwbaP (SKI12) was spun down at 16,000 g for 2 min and the supernatant was discarded. Cells were resuspended in 100 µl Lämmli sample buffer (0.065 M Tris-HCl pH 6.8, 2% SDS (w/v), 5% R-Mercaptoethanol (v/v), 10% Glycerin (v/v), 0.05% Bromophenol blue (w/v)) and lysed for 5 min at 95° C. After cooling down to room temperature, proteinase K (Gibco/Life Technologies) was added (final concentration 0.4 mg/ml) and incubated 1 h at 60° C. before loading equal amounts on a 12% sodium dodecylsulfate polyacrylamide gel electrophoresis (SDS-PAGE). To detect *S. Typhimurium* O-antigen, *Salmonella* 0 Antiserum Group B factors 1, 4, 5, 12 (Difco) was used. Visualisation of signals was carried out with goat-anti-rabbit-IgG-HRP conjugate (Santa Cruz) and ECL (Amersham) as recommended by the manufacturer. For staining, the method from Tsai and Frasch was used (Tsai and Frasch, Anal. Biochem. 119(1): 115-9, 1982).

The deletion of the gene encoding for the phosphogalactosyltransferase WbaP in *S. enterica* wild type led to an abolishment of O-antigen biosynthesis as visible in FIG. 2B. SDS-PAGE with subsequent staining of the glycoconjugates by silver as well as an SDS-PAGE followed by an immunoblot with *Salmonella* group B specific anti-O-antiserum show the typical lipopolysaccharide ladder pattern of the polymeric O-antigen for the *S. enterica* sv. *Typhimurium* wild type strain and the absence of this patter in the ΔwbaP strain.

This O-antigen negative *S. enterica* sv. *Typhimurium* ΔwbaP SKI12 was tested for its ability to display *C. jejuni* N-glycan on its cell surface. Plasmids pACYCpglmut or pACYC184 were introduced by electroporation. The glycoconjugates of the transformants were analysed as described in example 1. *C. jejuni* N-glycan could be detected in higher intensities in the lane containing the ΔwbaP strain compared to wildtype (FIG. 2A lane 4 vs lane 2). No *C. jejuni* N-glycan could be detected when the empty vector pACYC184 was present in the *S. enterica* sv. *Typhimurium* ΔwbaP SKI12. This demonstrates that in the ΔwbaP strain more *C. jejuni* N-glycan is transferred to lipid A core.

Example 3—Construction of an Altered *C. jejuni* pglmut Operon Leading to Increased *C. jejuni* N-Glycan Display on *Salmonella enterica* sv. *Typhimurium*

In *C. jejuni*, the N-glycan is synthesised as the heptasaccharide GalNAc5(Glc)-Bac, where Bac, the sugar at the reducing end, is 2,4-diacetamido-2,4,6-trideoxy-glucopyranose. In *E. coli* and *S. Typhimurium* Bac is not synthesised unless the *C. jejuni* N-glycan biosynthesis machinery is heterologously expressed. It was shown that in *E. coli* wild type cells co-expressing the *C. jejuni* N-glycan biosynthesis machinery two different kinds of N-glycan are synthesised, one with Bac at the reducing end and one with GlcNAc. This phenomenon could be attributed to the action of WecA, an UDP-GlcNAc: undecaprenylphosphate GlcNAc-1-phosphate transferase involved in glycolipid biosynthesis (Linton D. et al., Mol. Microbiol., 55(6):1695-703, 2005). As it is known that *Salmonella enterica* sv *Typhimurium* O-antigen ligase WaaL can transfer GlcNAc containing structures to lipid A core it was speculated that a GlcNAc-containing N-glycan could be a better substrate for WaaL than a Bac-containing N-glycan. A pgl$_{mut}$ operon was constructed that was deleted in the genes for bacillosamine biosynthesis, namely pglD,E,F,G. The genes encoding for PglE, F, G were completely deleted while the one encoding for PglD was partially deleted. The pglD open reading frame (ORF) in the altered pgl operon terminates after 270 base pairs while the full length ORF contains 612 base pairs. The procedure to construct this altered pgl$_{mut}$ operon was carried out using *E. coli* DH5a as host strain for plasmid propagation and is as follows: pACYCpglmut DNA was digested with Alw44I and SmaI, then the Alw44I overhang was filled in with the DNA polymerase I Klenow fragment and religated. The resulting operon was termed pACYCpgl3mut and was transformed into the ΔwbaP strain. The glycoconjugates of the resulting transformants were analysed as described in example 1. *C. jejuni* N-glycan could be detected in higher intensities in the lane containing the ΔwbaP strain with the pgl3mut operon than in the lane containing the ΔwbaP strain with the pglmut operon, when compared to wildtype (FIG. 2A lane 5 vs lane 4). All in all, the ΔwbaP strain with the pgl3mut shows the highest intensities when probed with the anti-*C. jejuni* N-glycan antiserum and therefore demonstrates the highest levels of *C. jejuni* N-glycan displayed on *Salmonella enterica* sv *Typhimurium* lipid A core.

Example 4—Integration of the pgl3mut Operon into the Genome of the O-Antigen Negative *Salmonella enterica* sv *Typhimurium* ΔwbaP Strain For ensuring continuous display of the *C. jejuni* N-glycan on the *Salmonella enterica* sv *Typhimurium* ΔwbaP strain lipid A core in vivo, the pgl3mut operon was integrated into the genome of ΔwbaP strain SKI12 downstream of the pagC gene.

All cloning steps involving a suicide plasmid with the oriR6K were performed in *E. coli* CC118λpir. The final integrative suicide plasmid pKI15 was constructed in the following way: A 512 bp sequence homologous to the target region in the *Salmonella* genome was amplified by PCR with the primers 3' PagC Fw NotI and 3' PagC Rev SacII (sequence see table 1). The resulting DNA fragment was inserted with SacII and NotI into pSB377 and the plasmid was termed pKI14 after verification of the insert sequence. PKI15 was constructed by digesting pACYCpgl3mut DNA with BamHI and EheI while digesting pKI14 with BamHI and SmaI. The 11083 bp fragment cut from pACYCpgl3mut was then ligated with the pKI14 backbone. As electroporation of suicide plasmids into *Salmonella* strains is very inefficient, pKI15 or pKI14 were first introduced into *E. coli* Sm10λpir for conjugation by electroporation. Sm10λpir containing pKI15 or pKI14 was then conjugated with SKI12. For conjugation the equivalents of 4 OD600 of late log-phase cultures of Sm10λpir containing pKI15 and SKI12 were spun down and washed three times with 1 ml LB. The pellets were resuspended in 100 µl LB, combined and spread with a diameter of 3 cm onto an LB agar plate that was then incubated over night at 37° C. The bacteria were washed off the plate in the following morning with 1 ml LB and several dilutions plated on LB (+strep+tet) selecting for conjugants. The resulting strains were called SKI34 (SKI12::pKI14) and SKI35 (SKI12::pKI15).

Figure 4:
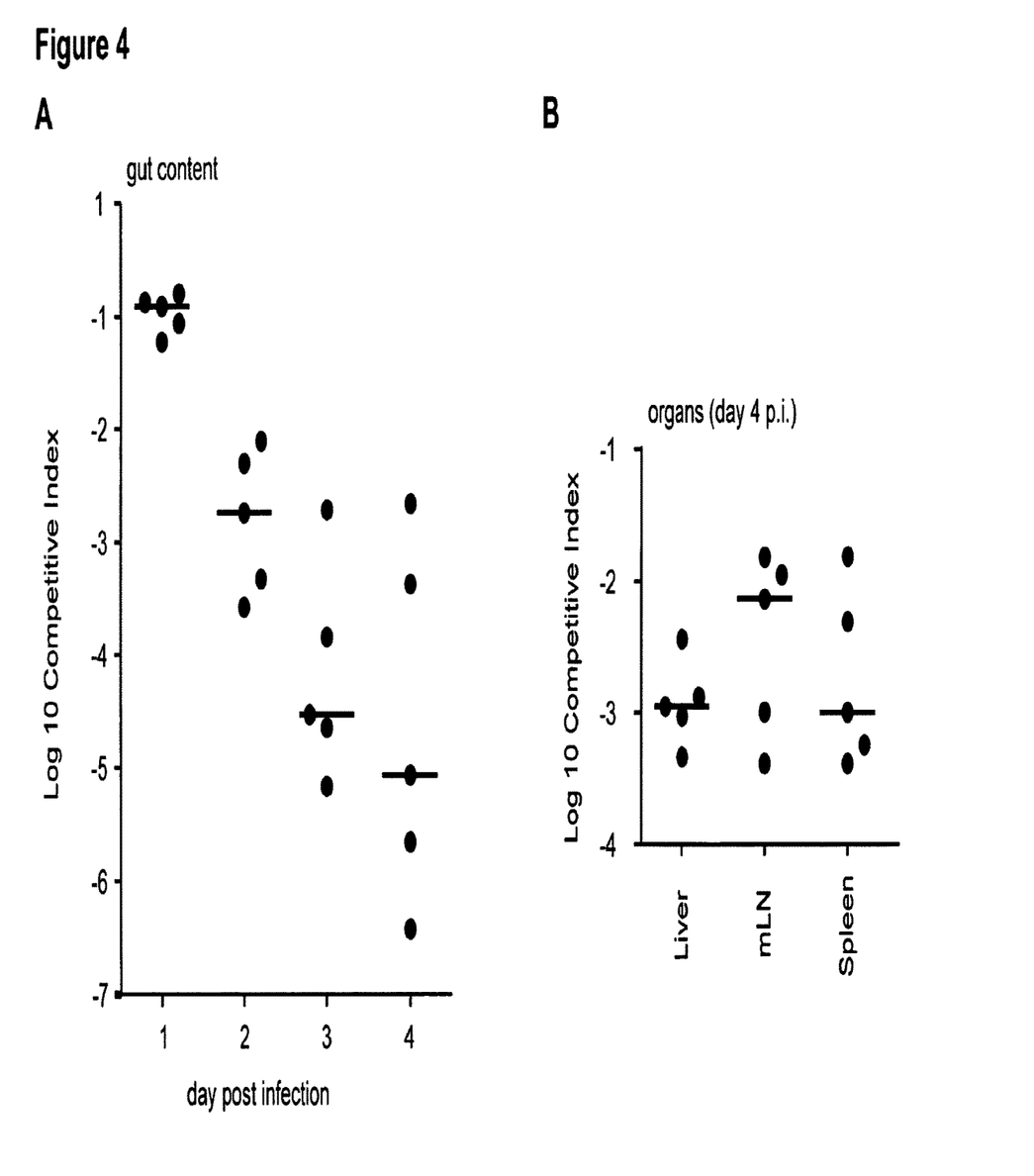
FIG. 4 demonstrates a reduced colonisation ability for *S. Typhimurium* ΔwbaP in a co-infection experiment with *S. Typhimurium* wild type.

To test for *C. jejuni* N-glycan on lipid A core of the O-antigen-negative strains containing either the integrated pgl3mut cluster or the integrated empty vector as a negative control, whole cell extracts of SKI34 and SKI35 were prepared and analysed as described in example 1. FIG. 2C is an immunoblot detected with anti-*C. jejuni* N-glycan antiserum which shows intense signals in lane 2 containing SKI35 but no signal for lane 1 containing SKI34. This demonstrates efficient transfer of *C. jejuni* N-glycan to *Salmonella enterica* sv *Typhimurium* lipid A core from an integrated pgl3mut operon.

Example 5—Immunogenicity of the Glycan Encoded by the $Pgl3_{mut}$ Operon

In order to investigate the immunogenicity of the $pgl3_{mut}$-encoded glycan mice were infected with heat-inactivated bacteria SKI12+$pMLpgl3_{mut}$ and their sera were tested for anti-*C. jejuni* N-glycan antibodies. The experiment was carried out as follows:

Mouse Infection Experiments

*Salmonella* infections were performed in individually ventilated cages at the RCHCI, Zurich, as previously described (Stecher, Hapfelmeier et al., Infection Infect Immun. 2004 July; 72(7):4138-50 2004). For the intravenous infection mice were injected into the tail vein with $5\times10^5$ CFU of heat-inactivated *S. Typhimurium* SL1344ΔwbaP (SKI12) carrying pMLBAD (control) or $pMLpgl3_{mut}$. After analysis of the sera at day 29 post infection mice were re-injected with the same bacterial strains at day 36 and sera were analysed on day 50.

Analysis of Mouse Sera

Mouse sera were analysed for production of anti-*C. jejuni* N-glycan antibodies by immunoblot against whole cell extracts of *C. jejuni* 81-176 and 81-176pglB (negative control). *C. jejuni* 81-176 μg/B does not produce glycosylated proteins and served as negative control. Whole cell extracts were prepared by harvesting *C. jejuni* from plates of confluent bacterial growth with 1 ml PBS. After adjusting the samples with PBS to the same optical density cells were collected by centrifugation for 2 min at 16000×g at room temperature. Cells were lysed for 5 min at 95° C. in Lämmli sample buffer (0.065 M Tris-HCl pH 6.8, 2% SDS (w/v), 5% β-Mercaptoethanol (v/v), 10% Glycerin (v/v), 0.05% Bromophenol blue (w/v)) added to the same final volumes as determined before with PBS to give the same amount of cells in each sample. This was confirmed by separating equal volumes of each sample by SDS-PAGE followed by staining of proteins with Coomassie blue. Additionally, glycosylated and unglycosylated protein AcrA was used for visualising an immune response against *C. jejuni* N-glycan. For analysis of mouse sera equal volumes of the whole cell extracts as well as equal amounts of glycosylated and unglycosylated AcrA were separated by SDS-PAGE followed by transfer of the proteins to a polyvinylidenfluorid membrane for immunoblot detection. The mouse sera served as primary antisera in the first incubation step. Bound IgG were identifed by an anti-mouse-IgG-HRP conjugate (Bethyl Laboratories). Detection was performed with ECL (Amersham) according to the manufacturer.

FIG. 1D) shows the presence of anti-*C. jejuni* N-glycan-IgG in mouse sera 61 days after re-infection. The antibodies did not recognise unglycosylated AcrA or unglycosylated protein extracts from *C. jejuni* and thereby prove specificity for the glycan. No *C. jejuni* N-glycan-specific reaction could be observed with sera of mice infected with the control strains (data not shown).

Example 6—Attenuated Phenotype of *S. Typhimurium* ΔwbaP

The attenuation of *S. Typhimurium* ΔwbaP was tested in several in vitro and an in vivo approach. The in vitro approach consisted of testing the mutant as well as the wildtype for their serum resistance, motility and resistance to the antimicrobial peptide mimic polymyxin B. The colonisation ability of ΔwbaP was analysed in an in vivo co-infection experiment.

Analysis of Serum Resistance

Bactericidal activity of complement was tested essentially as described (Bengoechea, Najdenski et al. 2004). In brief, serovar *Typhimurium* wbaP::cat (SKI11), M939, a kanamycin-resistant derivative of serovar *Typhimurium* wild type SL1344 strain (aph integrated downstream of sopE) and cells from serovar *Typhimurium* ΔwbaP::pKI9 (SKI33) taken from exponentially growing cultures were mixed in equal amounts ($3\times10^8$ cfu/ml for M393; $4\times10^8$ cfu/ml for SKI11 and SKI33) and diluted $5\times10^4$ fold before use in sterile 1×PBS. This diluted bacterial culture was mixed 1:1 with 20% human serum containing no antibodies against serovar *Typhimurium* LPS and incubated at 37° C. with slight agitation. Aliquots were taken at 0, 15 and 30 min after mixing and complement activity was quenched by adding Brain Heart Infusion Broth. The aliquots were kept on ice until plating on LB (strep, kan) selecting for wild type, LB (Sm, Cam) selecting for wbaP::cat and LB (Sm, Tet) to determine ΔwbaP::pKI9 CFU. The same experiment was carried out using serum where complement was heat-inactivated at 56° C. for 30 min. Data is shown as means of log CFU±standard deviations. FIG. 3A shows the decreased serum resistance of *S. Typhimurium* ΔwbaP when compared to wildtype: After 30 min of incubation with 20% human serum the counts for ΔwbaP were sixty times less than at the beginning of the incubation period. FIG. 3B depicts the same strains incubated with heat-inactivated serum as negative control.

Swimming Motility Assay

Because motility of bacteria is a known virulence factor motility of bacteria was tested on soft agar plates (0.3% (w/v) agar, 5 g/l NaCl, 10 g/l Bacto tryptone). 1 μl of overnight cultures of serovar *Typhimurium* wild type (SL1344), serovar *Typhimurium* ΔwbaP (SKI12), serovar *Typhimurium* ΔwbaP::pKI9 (SKI33) or serovar *Typhimurium* fliGHI::Tn10 (M933) were spotted in the middle of plates and motility was quantified by measuring the diameter of the halo visible after 4.75 h and 9.5 h of incubation at 37° C. Each experiment was carried out in triplicate on two different occasions and data are shown as means±standard deviations. As visible in FIG. 3C motility was strongly decreased in ΔwbaP (SKI12) when compared to wildtype but still higher than in the non-motile control fliGHI::Tn10.

Analysis of Polymyxin B Resistance

The equivalent of 1 $OD_{600}$/ml of exponentially growing cultures from serovar *Typhimurium* wild type SL1344 strain or serovar *Typhimurium* ΔwbaP (SKI12) was spun down, resuspended in 150 μl cold sterile 1×PBS and diluted $5\times10^6$ fold before use. For the assay 45 μl of the diluted cultures were mixed with 5 μl of Polymyxin B (Sigma, 1 μg/ml final concentration) or 5 μl PBS and incubated for 1 h at 37° C. under slight agitation. After addition of 80 μl LB bacteria were plated on LB-agar plates containing streptomycin. The survival efficiency was calculated by dividing the CFU (colony forming units) of peptide-treated culture by the CFU of untreated culture multiplied by 100. The assay was performed in triplicate on two independent experiments and data are shown as means±standard deviations. Decreased polymyxin B resistance of *S. Typhimurium* ΔwbaP compared to wildtype is evidenced in FIG. 3D.

Colonisation Ability of ΔwbaP in a Co-Infection Experiment

The colonisation ability of *S. Typhimurium* ΔwbaP was tested in a co-infection experiment in which mice were infected intragastrically with the ΔwbaP mutant as well as the wild type strain. C57BU6 mice (SPF; colony of the RCHCI, Zurich) were pretreated by gavage with 20 mg of streptomycin. 24 h later the mice were inoculated with $5 \times 10^7$ CFU of serovar *Typhimurium* strain or mixtures of strains as indicated. Bacterial loads (CFU) in fresh fecal pellets, mesenteric lymph nodes (mLNs), spleen, and cecal content were determined by plating on MacConkey agar plates (50 µg/ml streptomycin) as previously described (Barthel, Hapfelmeier et al. 2003). The competitive indices (CI) were determined according to the formula CI=(mutant/wild type) output/(mutant/wild type) input after plating. A co-infection experiment of serovar *Typhimurium* wild type (M939) and ΔwbaP strain (SKI11) was performed. 5 streptomycin-treated mice were infected with a 1:2 mixture (total $5 \times 10^7$ CFU) intragastrically of the ΔwbaP strain (SKI11) and wild type strain. The ratio of the 2 strains (CI; competitive index, see Materials and Methods) was determined in the feces at day 1, 2 and 3 p.i. A decrease of ΔwbaP counts compared to wild type was detected (one log scale per day) and proved that the ΔwbaP strain (SKI11) had indeed a severe competitive defect in comparison to wild type serovar *Typhimurium* strain in the intestinal tract ($p > 0.05$; FIG. 4A). Moreover, the CI of the two strains at systemic sites (mLN, liver, spleen) at day 4 p.i. also demonstrated a significant competitive defect of serovar *Typhimurium* ΔwbaP (SKI12). Nevertheless, the defect was less pronounced than in the intestine (FIG. 4B).

TABLE 1

Strains, plasmids and primers for wbaP deletion used in this work

| Strain | Genotype and phenotype | Source or reference |
|---|---|---|
| *Salmonella enterica* sv Typhimurium strains | | |
| SL1344 | wild type; strep$^R$ | Hoiseth, S. K. and B. A. Stocker, Nature 291:238-239, 1981 |
| SKI11 | SL1344ΔwbaP::cat; strep$^R$, cam$^R$ | this study |
| SKI12 | SL1344ΔwbaP; strep$^R$ | this study |
| SKI34 | SKI12::pKI14; strep$^R$, tet$^R$ | this study |
| SKI35 | SKI12::pKI15; strep$^R$, tet$^R$ | this study |
| *Escherichia coli* strains | | |
| DH5a | SupE44 ΔlacU169 (Φ80lacZΔM15) hsdR17 recA1 endA1 gyrA96 thi-1 relA1 | Hanahan, D., J. Mol. Biol., 5,166(4):557-80, 1983 |
| CC118 λpir | Δ(ara-leu), araD, ΔlacX74, galE, galK, phoA20, thi-1, rpsE, rpoB, argE(Am), recA, λpir | Herrero, M., V. de Lorenzo, and K. N. Timmis. J Bacteriol 172:6557-6567. |
| Sm10λpir | thi thr leu tonA lacY supE recA::RP4 2-Tc::Mu λpir, kan$^R$ | Miller, V. L. and J. J. Mekalanos. J. Bacteriol. 170:2575-2583, 1988. |
| Plasmids | | |
| Plasmid | Genotype | Source or reference |
| pSB377 | tet$^R$ oriR6K | Mirold et al., Proc. Natl. Acad. Sci. USA, 96:9845-9850, 1999. |
| pKD3 | bla FRT cat FRT PS1 PS2 oriR6K | Datsenko, K. A. and B. L. Wanner, Proc. Natl. Acad. Sci. USA, 97:6640-6645, 2000. |
| pKD46 | bla P$_{BAD}$ gam bet exo pSC101 oriTS | Datsenko, K. A., and B. L. Wanner, Proc. Natl. Acad. Sci. USA, 97:6640-6645, 2000. |
| pCP20 | bla cat cI857 λP$_R$ flp pSC101 oriTS | Datsenko, K. A., and B. L. Wanner, Proc. Natl. Acad. Sci. USA, 97:6640-6645, 2000 |

TABLE 1-continued

Strains, plasmids and primers for wbaP deletion used in this work

| | | |
|---|---|---|
| pACYC184 | Cm$^R$, Tc$^R$, ori p15A | New England Biolabs |
| pACYCpgl$_{mut}$ | Cm$^R$, ori p15A; *C. jejuni* pgl cluster with pglB$^{W458A, D459A}$ cloned in pACYC184 | Science, 298(5599):1790-3, 29. Nov. 2002 |
| pACYCpgl3$_{mut}$ | Cm$^R$, on p15A; *C. jejuni* pgl cluster with PglB$^{W458A, D459A}$ cloned in pACYC184, deletion of pglE, F, G and 3'- half of pglD | This study |
| pKI14 | Tet$^R$, oriR6K, 500 bp region 3' of PagC cloned in pSB377 | This study |
| pKI15 | Te$^R$, oriR6K, *C. jejuni* pgl3mut cluster with pglB$^{W458A, D459A}$ cloned into pKI15 | This study |

Primers for wbaP deletion

| | |
|---|---|
| RfbP H1P1 | CTTAATATGCCTATTTTATTTACATTATGCAC GGTCAGAGGGTGAGGATTAAGTGTAGGCTGGA GCTGCTTC (SEQ ID NO: 4) |
| RfbP H2P2 | GATTTTACGCAGGCTAATTTATACAATTATTA TTCAGTACTTCTCGGTAAGCCATATGAATATC CTCCTTAGTTCCTATTCC (SEQ ID NO: 5) |

Primers for pgl3$_{mut}$ Integration

| | |
|---|---|
| 3' PagC Fw NotI | AAGCGGCCGCGCATAAGCTATG CGGAAGGTTC (SEQ ID NO: 6) |
| 3' PagC Rev SacII | ACCGCGGGACACTGAGGTAATA ACATTATACG (SEQ ID NO: 7) |

---

We claim:

1. A method of using *Salmonella enterica*, including but not limited to live *Salmonella enterica*, for preparing a medicament, including but not limited to a vaccine, wherein the *Salmonella enterica* comprises at least one pgl operon of *Campylobacter jejuni* and further comprises at least one N-glycan of *Campylobacter jejuni* on its cell surface, wherein one or more genes for bacillosamine biosynthesis are inactivated by mutation or partial or complete deletion.

2. The method of use of claim 1 for preparing a medicament, including but not limited to a vaccine for the prevention or treatment of *Campylobacter jejuni* and optionally *Salmonella* infections.

3. The method of use of claim 2 wherein the infections to be treated are infections in livestock, including but not limited to cattle and poultry.

4. A method for treating or preventing *C. jejuni* and optionally *Salmonella* infections, comprising administration of *Salmonella enterica*, via a delivery medium including but not limited to pharmaceutical composition, food or feed, to a human or animal in need thereof in a physiologically active amount, wherein the *Salmonella enterica* comprises at least one pgl operon of *Campylobacter jejuni* and further comprises at lest one N-glycan of *Campylobacter jejuni* on its cell surface, and wherein one or more genes for bacillosamine biosynthesis are inactivated by mutation or partial or complete deletion.

* * * * *

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: consensus sequon for N-glycosylation
<220> FEATURE:
<221> NAME/KEY: VARIANT
<222> LOCATION: (1)..(1)
<223> OTHER INFORMATION: may be replaced by Glu
<220> FEATURE:
<221> NAME/KEY: VARIANT
<222> LOCATION: (2)..(2)
<223> OTHER INFORMATION: may be replaced by Arg, Asn, Asp, Cys, Gln,
      Glu, Gly, His, Ile, Leu, Lys, Met, Phe, Ser, Thr, Trp, Tyr, or Val
<220> FEATURE:
<221> NAME/KEY: VARIANT
<222> LOCATION: (4)..(4)
<223> OTHER INFORMATION: may be replaced by Arg, Asn, Asp, Cys, Gln,
      Glu, Gly, His, Ile, Leu, Lys, Met, Phe, Ser, Thr, Trp, Tyr, or Val
<220> FEATURE:
<221> NAME/KEY: VARIANT
<222> LOCATION: (5)..(5)
<223> OTHER INFORMATION: may be replaced by Thr

```
<400> SEQUENCE: 1

Asp Ala Asn Ala Ser
1               5

<210> SEQ ID NO 2
<211> LENGTH: 20
<212> TYPE: PRT
<213> ORGANISM: Artificial Sequence
<220> FEATURE:
<223> OTHER INFORMATION: Signal sequence for targeting to outer membrane

<400> SEQUENCE: 2

Met Lys Lys Ile Leu Leu Ser Val Leu Thr Thr Phe Val Ala Val Val
1               5                   10                  15

Leu Ala Ala Cys
            20

<210> SEQ ID NO 3
<211> LENGTH: 4
<212> TYPE: PRT
<213> ORGANISM: Artificial Sequence
<220> FEATURE:
<223> OTHER INFORMATION: LAAC motif of signal sequence

<400> SEQUENCE: 3

Leu Ala Ala Cys
1

<210> SEQ ID NO 4
<211> LENGTH: 72
<212> TYPE: DNA
<213> ORGANISM: Artificial Sequence
<220> FEATURE:
<223> OTHER INFORMATION: primer RfbP H1P1

<400> SEQUENCE: 4
cttaatatgc ctattttatt tacattatgc acggtcagag ggtgaggatt aagtgtaggc      60
tggagctgct tc                                                         72

<210> SEQ ID NO 5
<211> LENGTH: 82
<212> TYPE: DNA
<213> ORGANISM: Artificial Sequence
<220> FEATURE:
<223> OTHER INFORMATION: primer RfbP H2P2

<400> SEQUENCE: 5
gattttacgc aggctaattt atacaattat tattcagtac ttctcggtaa gccatatgaa      60
tatcctcctt agttcctatt cc                                              82

<210> SEQ ID NO 6
<211> LENGTH: 32
<212> TYPE: DNA
<213> ORGANISM: Artificial Sequence
<220> FEATURE:
<223> OTHER INFORMATION: primer 3' PagC Fw NotI

<400> SEQUENCE: 6
aagcggccgc gcataagcta tgcggaaggt tc                                   32

<210> SEQ ID NO 7
<211> LENGTH: 32
<212> TYPE: DNA
```

```
<213> ORGANISM: Artificial Sequence
<220> FEATURE:
<223> OTHER INFORMATION: primer 3' PagC Rev SacII

<400> SEQUENCE: 7
accgcgggac actgaggtaa taacattata cg                                32
```